United States Patent [19]

Tagawa et al.

[11] Patent Number: 5,556,948
[45] Date of Patent: Sep. 17, 1996

[54] PHOSPHOLIPID DERIVATIZED WITH PEG BIFUNCTIONAL LINKER AND LIPOSOME CONTAINING IT

[75] Inventors: Toshiaki Tagawa; Kaoru Awane, both of Yokohama; Kazuhiro Nagaike, Sagamihara, all of Japan

[73] Assignee: Mitsubishi Chemical Corporation, Tokyo, Japan

[21] Appl. No.: 182,832

[22] Filed: Jan. 19, 1994

[30] Foreign Application Priority Data

Jan. 22, 1993 [JP] Japan .................... 5-027651

[51] Int. Cl.$^6$ .................... C07K 17/02; C07K 16/00; C07F 9/10; A61K 9/127
[52] U.S. Cl. .................... 530/391.9; 530/391.1; 424/450; 424/178.1; 548/119
[58] Field of Search .................... 424/450, 178.4; 548/119; 530/391.9, 391.1

[56] References Cited

U.S. PATENT DOCUMENTS

| | | |
|---|---|---|
| 4,429,008 | 1/1984 | Martin et al. . |
| 5,045,451 | 9/1991 | Lihr et al. .................... 435/7.23 |
| 5,059,421 | 10/1991 | Loughrey et al. . |
| 5,264,221 | 11/1993 | Tagawa et al. . |

FOREIGN PATENT DOCUMENTS

| | | |
|---|---|---|
| 2069244 | 11/1992 | Canada . |
| 0354855 | 2/1990 | European Pat. Off. . |
| 0448126 | 9/1991 | European Pat. Off. . |
| 0520499 | 12/1992 | European Pat. Off. . |
| 0526700 | 2/1993 | European Pat. Off. . |
| 1-249717 | 10/1989 | Japan . |
| WO83/02069 | 6/1983 | WIPO . |
| WO90/04384 | 5/1990 | WIPO . |
| WO90/07924 | 7/1990 | WIPO . |
| WO91/05546 | 5/1991 | WIPO . |
| WO92/06192 | 4/1992 | WIPO . |

OTHER PUBLICATIONS

Borrebaeck, Journal of Immunological Methods, vol. 123, pp. 157–165 (1989).

Waldmann, Science, vol. 252, pp. 1657–1662 (1991).

Hermentin et al., Behring Inst. Mitt., No. 82, pp. 197–215 (1988).

Canevari et al., Ann Oncol., vol. 5/8, pp. 698–701 (1994).

Antisense Research and Development, vol. 2, No. 3, pp. 187–197, 1992, S. M. Sullivan, et al., "Inhibition of Human Immunodeficiency Virus–1 Proliferation by Liposome–Encapsulated Sense DNA to the 5' TAT Splice Acceptor Site".

Biochimica et Biophysica Acta, vol. 1061, pp. 56–64, 1991, T. M. Allen, et al., "Uptake of Liposomes by Cultured Mouse Bone Marrow Macrophages: Influence of Liposome Composition and Size".

Proc. Natl. Acad. Sci. USA, vol. 87, pp. 5744–5748, Aug. 1990, K. Maruyama, et al., "Lipid Composition is Important for Highly Efficient Target Binding and Retention of Immunoliposomes".

Nature, vol. 288, pp. 602–604, Dec. 1980, L. D. Leserman, et al., "Targeting to Cells of Fluorescent Liposomes Covalently Coupled with Monoclonal Antibody of Protein A".

The Journal of Biological Chemistry, vol. 255, No. 17, pp. 8015–8018, Sep. 10, 1980, A. Huang, et al., "Monoclonal Antibody Covalently Coupled with Fatty Acid".

The Journal of Biological Chemistry, vol. 257, No. 1, pp. 286–288, Jan. 10, 1982, F. J. Martin, et al., "Irreversible Coupling of Immunoglobulin Fragments to Preformed Vesicles".

Federation of European Biochemical Societies, vol. 284, No. 2, pp. 263–266, Jun. 1991, A. Mori, et al., "Influence of the Steric Barrier Activity of Amphipathic Poly(Ethyleneglycol) and Ganglioside GM1 on the Circulation Time of Liposomes and on the Target Binding of Immunoliposomes In Vivo".

Cancer Research, vol. 47, pp. 4471–4477, Aug. 15, 1987, H. Konno, et al., "Antitumor Effect of Adriamycin Entrapped in Liposomes Conjugated with Anti–Human α–Fetoprotein Monoclonal Antibody".

Cancer Research, vol. 43, pp. 5328–5334, Nov. 1983, Y. Hashimoto, et al., "Antitumor Effect of Actinomycin D Entrapped in Liposomes Bearing Subunits of Tumor–Specific Monoclonal Immunoglobulin M Antibody".

Biochimica et Biophysica Acta, vol. 1066, pp. 29–36, 1991, T. M. Allen, et al., "Liposomes Containing Synthetic Lipid Derivatives of Poly(Ethylene Gylcol) Show Prolonged Circulation Half–Lives In Vivo".

Journal of Liposome Research, vol.2, No.3, pp. 321–334, 1992, A. L. Klibanov, et al., "Long–Circulating Liposomes: Development and Perspectives".

Advanced Drug Delivery Reviews, vol.3, pp. 343–389, 1989, S. Wright, et al., "Antibody–Directed Liposomes as Drug–Delivery Vehicles".

Cancer Research, vol.52, pp. 4817–4820, Sep. 1, 1992, I. Ahmad, et al., "Antibody–Mediated Specific Binding and Cytotoxicity of Liposome–Entrapped Doxorubin to Lung Cancer Cells In Vitro".

Biochimica et Biophysica Acta, vol. 1062, pp. 142–148, 1991, A. L. Klibanov, et al., "Activity of Amphipathic Poly(Ethylene Glycol) 5000 to Prolong the Circulation Time of Liposomes Depends on the Liposome Size and is Unfavorable for Immunoliposome Binding to Target".

Federation of European Biochemical Societies Letters, vol.268, No. 1, pp. 235–237, Jul. 1990, A. L. Klibanov, et al. "Amphipathic Polyethyleneglycols Effectively Prolong the Circulation Time Liposomes".

*Primary Examiner*—Kay K. A. Kim
*Attorney, Agent, or Firm*—Oblon, Spivak, McClelland, Maier, & Neustadt, P.C.

[57] ABSTRACT

A phospholipid derivative of the following formula (I):

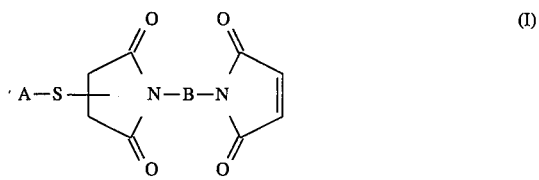

wherein A is a residue of a phospholipid having a phosphatidylethanolamine moiety, and B is a linking group having a polyalkylene glycol moiety.

5 Claims, 5 Drawing Sheets

PHOSPHOLIPID DERIVATIZED WITH PEG BIFUNCTIONAL LINKER AND LIPOSOME CONTAINING IT

The present invention relates to a novel phospholipid derivative and a liposome containing it. Particularly, it relates to a novel phospholipid derivative having a polyalkylene glycol moiety having a maleimide group.

A liposome being a lipid vesicle is capable of containing many substances irrespective of whether such substances are water-soluble or hydrophobic and thus is expected to be a prospective carrier especially for a drug delivery system (DDS).

In recent years, for the purpose of imparting a functionality to the liposome in addition to the inherent properties thereof, an attempt has been made to bond (or introduce) a functional compound such as a protein, a peptide, a sugar or a hydrophilic polymer to the liposome surface.

On the other hand, many studies have been made to overcome general drawbacks of a liposome, such as agglomeration and non-specific capture by a reticuloendothelial system organ such as liver or spleen, and it has been found effective to bond a polyethylene glycol to the liposome (Japanese Unexamined Patent Publications No. 249717/1989 and No. 149512/1990, FEBS letters, 268,235 (1990)).

Further, for the purpose of imparting the function of protein and the properties of polyethylene glycol, methods have been proposed to produce a liposome which contains both a protein and a polyethylene glycol (BBA, 1062:142 (1991), and Japanese Unexamined Patent Publication No. 346918/1992).

The former is a method which comprises solubilizing a lipid-modified antibody, a phospholipid, cholesterol and a lipid derivative of polyethylene glycol by means of a surfactant, followed by removing the surfactant by dialysis, to obtain a liposome. However, it is difficult to remove the surfactant completely, and the product will hardly be useful as a drug. Further, it is necessary to carry out the dialysis for a long period of time at a temperature higher than the phase transfer temperature of the lipid, whereby a useful lipid is rather limited especially when an unstable protein is employed for the production.

The latter is a method which comprises preparing a liposome containing maleimide groups, then bonding a protein having thiol groups and further bonding a polyethylene glycol having thiol groups to excess maleimide groups. While the protein can be bonded under a mild condition, this method has a problem that the production process is cumbersome, since it involves a two step reaction, and it is difficult to independently control the amount of each component to be bonded.

The present inventors have conducted a study to solve such problems of conventional liposomes containing both a protein and a polyalkylene glycol and as a result, have found it possible to readily produce a liposome containing both a protein and a polyalkylene glycol by using, as a liposome-constituting component, a phospholipid derivative having a maleimide group at one end of a polyalkylene glycol and a phosphatidylethanolamine moiety at the other end. Further, it has been surprisingly found that the liposome containing such a phospholipid derivative can readily be micronized during the process for micronizing the liposome. The present invention has been accomplished on the basis of these discoveries.

Namely, the present invention provides a phospholipid derivative of the following formula (I) and a liposome containing such a derivative:

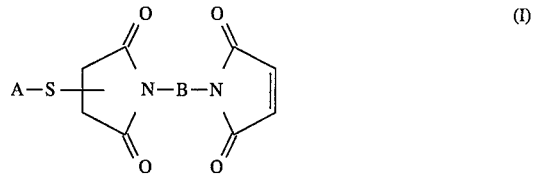

wherein A is a residue of a phospholipid having a phosphatidylethanolamine moiety, and B is a linking group having a polyalkylene glycol moiety.

Figure 1:
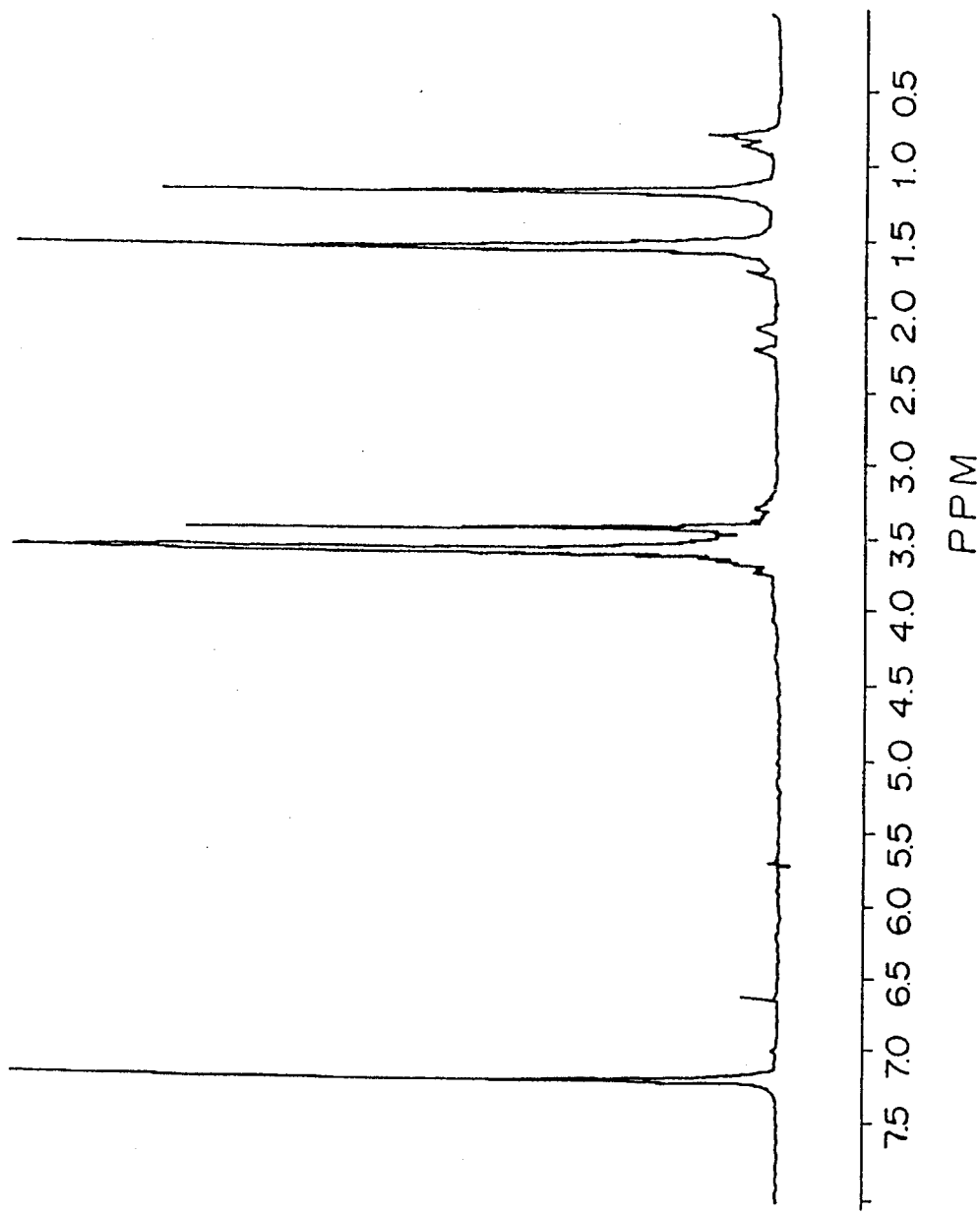
FIG. 1 is a graph showing the $^1$H-NMR chart of M-PEG-PE obtained in Example 1.

Now, the present invention will be described in detail.

The phospholipid derivative of the present invention is represented by the above formula (I). The residue of a phospholipid having phosphatidylethanolamine moiety for A, is not particularly limited so long as it is the one having a phosphatidylethanolamino group. However, it may preferably be a group of the following formula (II):

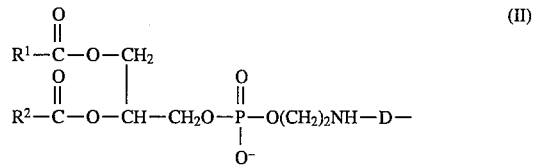

wherein each of $R^1$ and $R^2$ which are independent of each other, is a $C_{11}$–$C_{19}$ alkyl group such as a lauroyl group, a myristoyl group, a palmitoyl group or a stearoyl group, or a $C_{11}$–$C_{19}$ alkenyl group such as an oleyl group, and D is a single bond, or a $C_1$–$C_{11}$ linking group such as —C=(NH$_2^+$) (CH$_2$)$_{0-10}$—, —CO(CH$_2$)$_{0-10}$— or —CH$_2$(CH$_2$)$_{0-10}$—.

The linking group having a polyalkylene glycol moiety for B, is not particularly limited so long as it is the one having a polyalkylene glycol unit such as polyethylene glycol, polypropylene glycol, polytetramethylene glycol or polyhexamethylene glycol. However, it may preferably be a linking group of the following formula (III):

$$\text{-J-PEG-L-} \tag{III}$$

wherein each of J and L which are independent of each other, is a single bond, or a $C_1$–$C_{11}$ linking group such as —$CO(CH_2)_{0-10}$—, —$(CH_2)_{0-10}CO$—, —$NHCO(CH_2)_{0-10}$—, —$(CH_2)_{0-10}CONH$—, or —$CH_2(CH_2)_{0-10}$—, and PEG is a polyethylene glycol residue such as —$(CH_2CH_2O)_{11-455}$—.

Now, a process for producing the phospholipid derivative of the present invention will be described.

The phospholipid derivative of the present invention can be produced, for example, by reacting a lipid having a thiol group with a polyalkylene glycol having two maleimide groups.

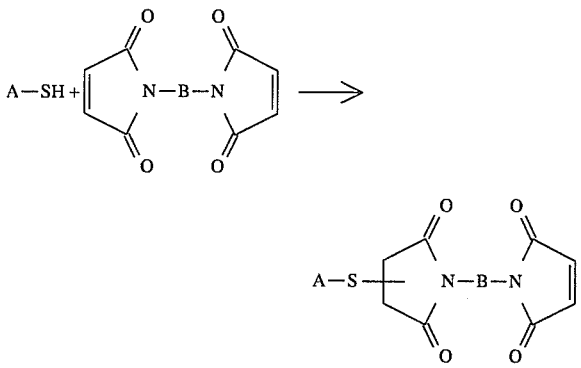

In the above formulas, A and B are as defined above.

Now, the process will be described sequentially in detail.

1. Preparation of the phospholipid having a thiol group (hereinafter sometimes referred to simply as "the thiol-modified phospholipid")

The thiol-modified phospholipid can be obtained by introducing a thiol group to phosphatidylethanolamine by means of a known amino group-modifying reaction. Namely, it can be produced by dissolving a Traunt reagent such as iminothiolane or a mercapto alkyl imidate and phosphatidylethanolamine in an organic solvent such as chloroform or chloroform/methanol (1/1 to 10/1) in the presence of a basic compound such as triethylamine or pyridine and reacting them at a temperature of from 20 to 40° C. under a condition of an inert gas such as nitrogen gas or argon gas. Otherwise, it can be prepared by means of a thiol carboxylic acid disclosed in Japanese Unexamined Patent Publication No. 72067/1989. Or, it may be synthesized by bonding a compound inherently containing a sulfur atom, such as N-succinimidyl-3-(2-pyridyldithio)propionate, to phosphatidylethanolamine, followed by reducing with a large excess amount of a reducing agent such as 2-mercaptoethanol.

The phosphatidylethanolamine to be used here, i.e. the phospholipid having a phosphatidylethanolamine moiety, for A in the above formula (I), is not particularly limited and may, for example, be natural phosphatidylethanolamine derived from e.g. yolk, dioleyl phosphatidylethanolamine, dimyristoyl phosphatidylethanolamine, dipalmitoyl phosphatidylethanolamine or distearoyl phosphatidylethanolamine, preferably dipalmitoyl phosphatidylethanolamine.

2. Preparation of the polyalkylene glycol having two maleimide groups (hereinafter sometimes referred to simply as "the maleimide PAG") The process will be described in detail with respect to a case wherein the polyalkylene glycol moiety is polyethylene glycol (hereinafter sometimes referred to simply as "PEG").

The polyethylene glycol derivative having two maleimide groups can be obtained, for example, by dissolving diaminopolyethylene glycol (available from Nippon Oil and Fats or Sigma) and at least a two-fold molar amount of a maleimide-modifying reagent such as N-(ε-maleimidocaproyloxy)succinimide in an organic solvent such as chloroform dehydrated by e.g. molecular sieve, in the presence of a basic compound such as triethylamine or pyridine and reacting them at a temperature of from 20° to 40° C. under an atmosphere of an inert gas such as nitrogen gas or argon gas.

In addition to N-(ε-maleimidocaproyloxy)succinimide, the maleimide-modifying reagent may, for example, be N-succinimidyl 4-(p-maleimidophenyl)butyrate, N-succinimidyl 4-(p-maleimidophenyl)propionate or N-(γ-maleimidobutyryloxy)succinimide, which is commonly used for the preparation of a maleimide derivative of an amino group.

The average molecular weight of the PEG moiety is usually from 500 to 20000, preferably from 2000 to 10000, more preferably from 2000 to 5000. As such PEG, SUNBRIGHT® VFM5001 (Nippon Oil and Fats) or Polyoxyethylenebisamine (Sigma) may specifically be mentioned.

3. Preparation of the compound of the present invention (hereinafter sometimes referred to simply as "M-PAG-PE")

M-PAG-PE can be prepared by adding and reacting the thiol-modified phospholipid dissolved in an organic solvent such as chloroform or chloroform/methanol (1/1 to 10/1) to the dimaleimide PAG dissolved in the same solvent in the presence of a basic compound such as triethylamine or pyridine at a temperature of from 0° to 40° C. under an atmosphere of an inert gas such as nitrogen gas or argon gas. Here, the thiol-modified phospholipid is gradually added, and its total amount is usually at most an equimolar amount, preferably at most ½ mol of the maleimide PAG.

Then, hexane or petroleum ether is added to the reaction solution of M-PAG-PE to precipitate a PAG-containing compound. The precipitate collected by filtration is dried and then dissolved in distilled water at a concentration not lower than the concentration where M-PAG-PE itself forms particles (micell) in the aqueous solution. Insoluble matters are filtered off, and while maintaining the concentration at the above specified level, the solution is subjected to molecular weight fractionation by e.g. an ultrafiltration method, a dialysis method or a gel filtration method to obtain M-PAG-PE. At that time, impurities such as unreacted (excess) dimaleimide PAG are removed. Further, if necessary, purification by silica gel column chromatography may further be carried out.

The phospholipid derivative of the present invention thus obtained can be converted to a liposome by a conventional method. The liposome may be formed by a conventional lipid component such as phosphatidylcholine or cholesterol, and M-PAG-PE, or may be formed by mixing such a conventional lipid component, M-PAG-PE and another lipid derivative having a polyethylene glycol moiety as disclosed in e.g. Japanese Unexamined Patent Publication No. 249717/1989 or No. 149512/1990 or FEBS letters, 268,235 (1990).

The phosphatidylcholine useful as the lipid component is not particularly limited and may, for example, be natural phosphatidylcholine derived from e.g. yolk, dioleyl phosphatidylcholine, dimyristoyl phosphatidylcholine, dipalmitoyl phosphatidylcholine or distearyl phosphatidylcholine.

The respective components are used in such proportions that per mol of the phosphatidylcholine, the cholesterol is used in an amount of from 0.3 to 1 mol, preferably from 0.4 to 0.6 mol, and M-PAG-PE is used in an amount of from 0.001 to 0.4 mol, preferably from 0.02 to 0.1 mol. Further, when another lipid derivative having a polyethylene glycol moiety is incorporated, such another lipid derivative is used in an amount of not more than 0.4 mol per mol of the phosphatidylcholine.

Then, the lipid mixture having the solvent removed, may, for example, be hydrated and emulsified by a homogenizer, followed by freezing-thawing to obtain a multilamella liposome (MLV). Further, it may be subjected to super sonic treatment, high speed homogenizing or press-filtration with a membrane having uniform pores (Hope M. J. et al, Biochimica et Biophysica Acta, 812, 55 (1985)) to obtain a single lamella liposome (SUV) and to adjust the particle size to a proper level. Here, a preferred particle size is from 20 to 300 nm, more preferably from 30 to 200 nm.

Various drugs may be loaded into such a liposome. As such a drug, an antitumor drug such as adriamycin, daunomycin, mitomycin, cisplatin, vincristine, epirubicin, methotrexate, 5FU (5-fluorouracil) or acracinomycin, an aminoglucoside such as gentamicin, a β-lactam antibiotic such as sulpenisillin, a toxin such as ricin A or diphtheria toxin, or an antisense RNA against human immunodeficiency virus (HIV), hepatitis B virus, hepatitis C virus or ras gene, may, for example, be mentioned.

Loading of the drug into the liposome can be conducted by hydrating the lipid with an aqueous drug solution in the case of a water-soluble drug, or by mixing the drug and the lipid in a volatile organic solvent, followed by distilling the solvent off and hydrating the mixture of the drug and the lipid to incorporate the drug into the liposome, in the case of a lipophilic drug.

Further, for the purpose of imparting a functionality to liposome, it is preferred to bond (introduce) a protein, a peptide, a saccharide, a hydrophilic polymer, etc. to the surface of the liposome, as mentioned above. In the present invention, it is preferred to bond (introduce) various proteins including antibodies or growth factories such as fibroblast growth factor (FGF) and epitheliocyte growth factor (EGF). Particularly preferred are antibodies. The antibodies are those (such as IgA, IgG and IgM) which are reactive with the tissues, cells, bacteria or virus to be treated. For example, polyclonal antibodies of various animals, a mouse monoclonal antibody, a human-mouse chimeric antibody and a human monoclonal antibody may be employed.

To bond such a protein to the liposome, the double bond of the maleimide group of the liposome and the thiol group of the protein can be utilized. Introduction of a thiol group to the protein can be conducted by a method wherein a compound is employed which is commonly used for thiol-modification of a protein and which is reactive with an amino group of the protein, such as N-succinimidyl- 3-(2-pyridyldithio)propionate (SPDP) (Carlsson, J. et al., Biochem. J. 173, 723 (1978)) or iminothiolane, mercaptoalkylimidate (Traut, R. R. et al., Biochemistory, 12, 3266 (1973)). In the case where the protein is an antibody, a method may be employed wherein endogenous dithiol groups in the cystine residues are reduced to thiol groups.

When IgG is employed among antibodies, it may be subjected to F(ab')$_2$ modification by treatment with an enzyme such as pepsin, followed by reduction with e.g. dithiothreitol to obtain Fab', whereupon thiol groups formed in Fab' are subjected to the bonding reaction with the liposome (Martin, F. J. et al., Biochemistory, ,20, 4229 (1981)). In the case of IgM, J-chain may be reduced under a mild condition in accordance with a method of Miller et al. (J. Biol. Chem. 257, 286 (1965)), whereupon thiol groups of Fc moiety of IgMs thereby obtained, are subjected to the bonding reaction with the liposome.

The bonding of the liposome with such a protein can be accomplished by reacting them in a neutral buffer solution (pH 6.0 to 7.5) for from 2 to 16 hours.

To use the liposome of the present invention as a pharmaceutical composition, it may be administered by e.g. intravascular administration or local administration such as intravesical or intraperitoneal administration against various diseases. The dose may optionally be adjusted depending upon the pharmacological activities, the type of the drug, etc.

Now, the present invention will be described in further detail with reference to Examples. However, it should be understood that the present invention is by no means restricted to such specific Examples.

EXAMPLE 1

Preparation of M-PEG-PE

Preparation of thiol-modified phospholipid 21.8 mg of iminothiolane (manufactured by Sigma Company) was added to 100 mg of dipalmitoyl phosphatidylethanolamine dissolved in 11 ml of a mixture of chloroform/methanol (6/5). Then, 50 μl of triethylamine was further added thereto, and the mixture was stirred and reacted at room temperature in nitrogen gas until the ninhydrin reaction became negative. Formation of the thiol-modified phospholipid was confirmed by adding fluoresce maleimide (manufactured by Funakoshi) to a part of the reaction solution, reacting them at room temperature for 40 minutes and observing a fresh yellow fluorescent spot on a thin layer chromatography.

Preparation of dimaleimide PEG 810 mg of diamino polyethylene glycol (SUNBRIGHT® VFM5001 (manufactured by Nippon Oil and Fats); average molecular weight: 5000) was dissolved in 5 ml of chloroform dehydrated by a molecular sieve, and 100 mg of N-(ε-maleimidocaproyloxy)succinimide and 50 μl of triethyamine were added thereto. The mixture was stirred and reacted at room temperature in nitrogen gas. Formation of dimaleimide PEG was ascertained by confirming that the ninhydrin reaction became negative.

Bonding and purification

To 4 ml of the above dimaleimide PEG solution diluted to 30 ml with chloroform, 10 ml of the above thiolmodified phospholipidsolution was gradually added, and the mixture was stirred at room temperature for 3 hours under a nitrogen gas condition. To 20 ml of the reaction solution thus obtained, an adequate amount of hexane was added to form a precipitate containing M-PEG-PE. The precipitate was vacuum-dried, whereupon the weight was 330 mg. It was dissolved in 10 ml of distilled water, and insoluble substances were removed by centrifugal separation of 16000× g for 5 minutes. Further, the same amount of distilled water was added, and concentration-filtration was repeated by means of CENTRICON 100 (manufactured by Amicon) equipped with an ultra filter membrane with a molecule weight fraction of 100 k. By this purification process, PEG not combined with the lipid derivative, was filtered off.

Measurement by NMR

As shown by the $^1$H-NMR chart of the desired product in FIG. 1, a signal of 1.54 ppm of the alkyl chain proton of the phospholipid, a signal of 3.57 ppm attributable to —CH$_2$CH$_2$O— of PEG and a signal of 6.61 ppm attributable to the double bond of the maleimide, were confirmed.

REFERENCE EXAMPLE 1

As shown in Example 1, the phospholipid derivative of the present invention was considered to behave as a molecular aggregate in the aqueous solution. Therefore, the form of M-PEG-PE in the aqueous solution was studied.

M-PEG-PE dissolved in distilled water at a concentration of 0.5 mg/ml, was measured by a dynamic light scattering method (ELS-800, manufactured by Otsuka Denshi), whereby particles of 24.8 nm (g (GAMMA) distribution) were observed.

EXAMPLE 2

Measurement of maleimide

The maleimide content of M-PEG-PE obtained in Example 1 was determined by adding cysteine to the aqueous solution and quantitatively analyzing the SH amount consumed by the maleimide by means of 4,4'-dithiopyridine. Namely, an aqueous solution containing 1.1 mg/ml of M-PEG-PE was mixed in the following proportion, and the mixture was reacted at room temperature for 30 minutes.

| | |
|---|---|
| M-PEG-PE | 100 µl |
| 1 mM EDTA-containing 0.1 M phosphate buffer (pH 6.0) | 800 µl |
| 0.5 mM cysteine | 100 µl |

After the reaction, 40 µl of 5 mM 4,4'-dithiopyridine was added to 960 µl of the above solution, and the maleimide content was determined by comparing the change in the absorbance at 324 nm by the color developed by the reaction with the remaining cysteine, with that of the control sample (a mole absorbance coefficient of the developed color of 19800/M was employed).

As a result, a maleimide amount of 0.17 µmol per mg of M-PEG-PE was detected.

EXAMPLE 3

Preparation of liposome containing M-PEG-PE 50 mg of dipalmitoyl phosphatidylcholine, 14.6 mg of cholesterol, 10.7 mg of M-PEG-PE and 0.16 mg of FITC-DPPE (1,2-Dihecadecanoyl-sn-glycero-3-phospho[N-(5-fluoresceinthiocarbamoyl)]ethanolamine, manufactured by Sigma) as a fat-solble marker, were dissolved uniformly in chloroform, and the solvent was removed by an evaporator to form a lipid film. Further, the film was dried under reduced pressure by a vacuum pump for 2.5 hours, and then a 0.1M phosphate buffer solution (pH 6.0) and 1 ml of 1 mM EDTA were added thereto, the mixture was stirred and hydrated by a voltex mixer. Then, freezing-thawing was repeated five times by means of liquid nitrogen and warm bath of 65° C., to obtain a milky white multilamella liposome (MLV).

Figure 2:
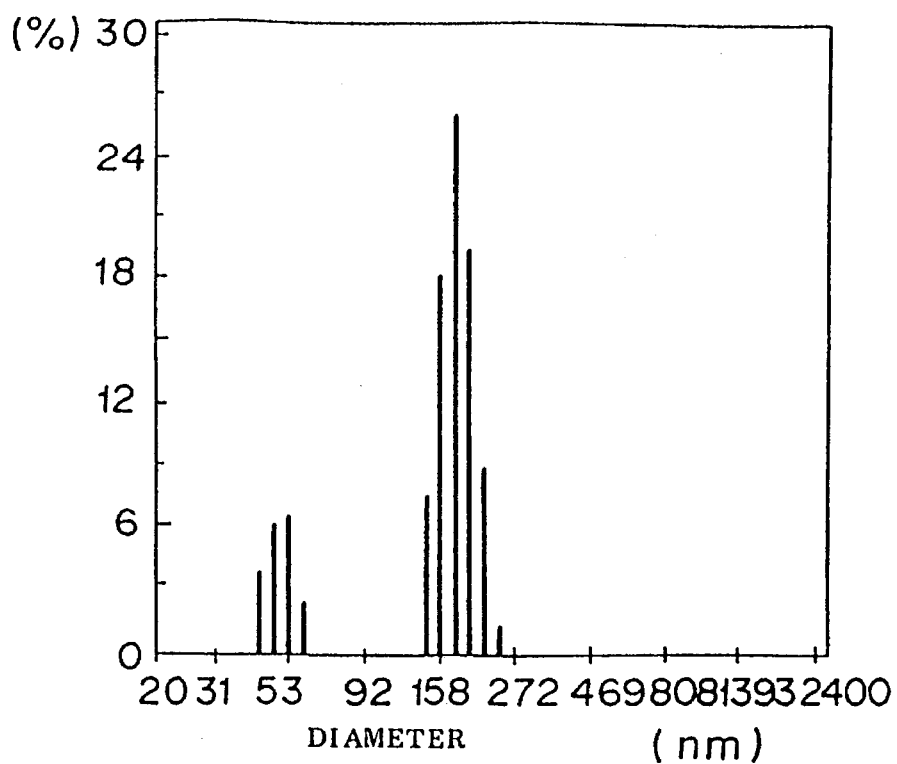
FIG. 2 is a graph showing the results of measurement of the particle size distribution of the M-PEG-PE-containing liposome prepared in Example 3 by a dynamic light scattering method.
Figure 3:
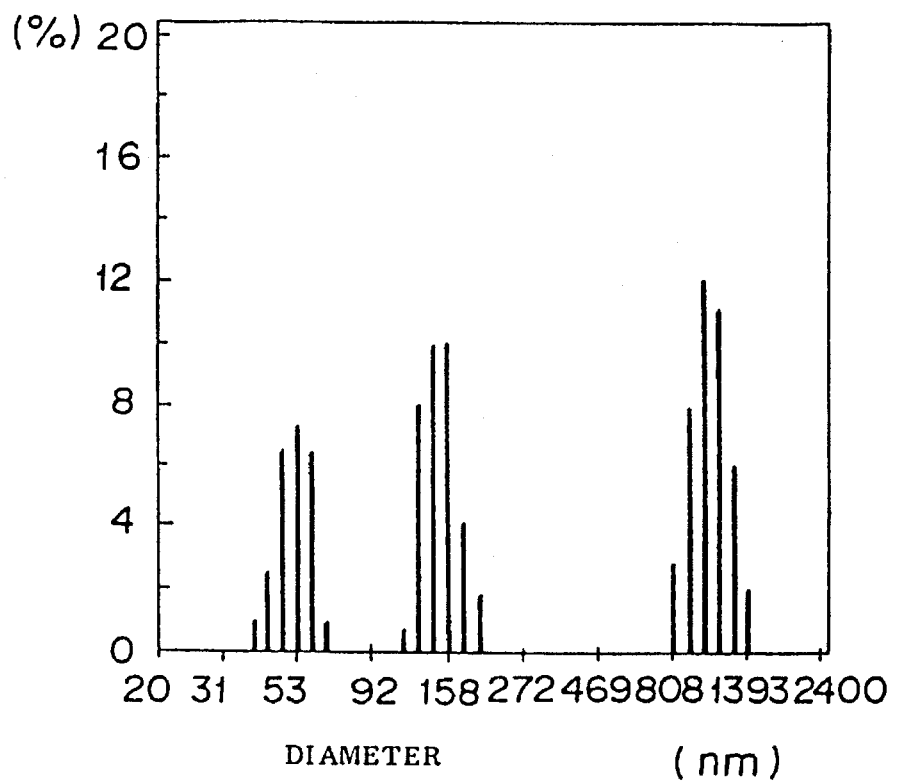
FIG. 3 is a graph showing the results of measurement of the particle size distribution of the liposome containing no M-PEG-PE, prepared in Comparative Example, by a dynamic light scattering method.

Then, 0.5 ml of the above MLV was adjusted to 1 ml with the above buffer solution and subjected to supersonic treatment for 10 minutes by a Probe-type sonicater (Sonifier 450, manufacture by Branson Company) at an output of 20%, to obtain a transparent small diameter liposome (SUV solution). FIG. 2 shows the particle size distribution of the liposome thus obtained, as measured by a dynamic light scattering method, it is shown that there was no inclusion of particles having a diameter of more than 1 µm. COMPARATIVE EXAMPLE MLV was prepared in the same manner as in Example 3 except that the lipid composition did not contain M-PEG-PE. Supersonic treatment for 10 minutes was repeated twice in the same manner, and then the particle size distribution was measured by a dynamic light scattering method. The results are shown in FIG. 3. Particles having a diameter of more than 1 µm were included, thus indicating that no adequate micronization was accomplished.

EXAMPLE 4

Bonding of an antibody to the M-PEG-PE-containing liposome

To an antitumor human monoclonal antibody (IgG; GAH disclosed in EP 0520499 A), 1/40 mol amount of pepsine (Cooper Biomedical) in 0.1M acetic acid buffer solution (pH 4.0), was added, and the mixture was reacted at 37° C. over night for digestion to obtain F(ab')$_2$.

Further, by chromatography separation with a cation exchange resin (Mono S, manufactured by Pharmacia), F(ab')$_2$ was isolated. The preparation was conducted by a linear gradient from 0M to 1.0M NaCl in a 0.1M acetic acid buffer solution (pH 4.0), to obtain F(ab')$_2$.

The buffer solution was changed to a 50 mM phosphate buffer solution (pH 7.5) and 1 mM EDTA in a PD-10 column (manufacture by Pharmacia) to obtain a solution having an antibody concentration of 2.4 mg/ml. Then, iminothiolane (3 mg/ml) was added thereto in an amount corresponding to 4 mol times of the antibody, and the mixture was reacted at 37° C. for one hour. Unreacted iminothiolane was removed by demineralization by a PD-10 column equilibrated with a 0.1M phosphate buffer solution (pH 6.0) and 1 mM EDTA, to obtain 1.9 mg/ml of a thiolmodified antibody.

To 0.7 ml of this antibody, 0.42 ml of the SUV liposome obtained in Example 3, was added, and the mixture was shaked at room temperature over night to obtain an immunoliposome.

EXAMPLE 5

Reactivity to the target cells

Figure 4:
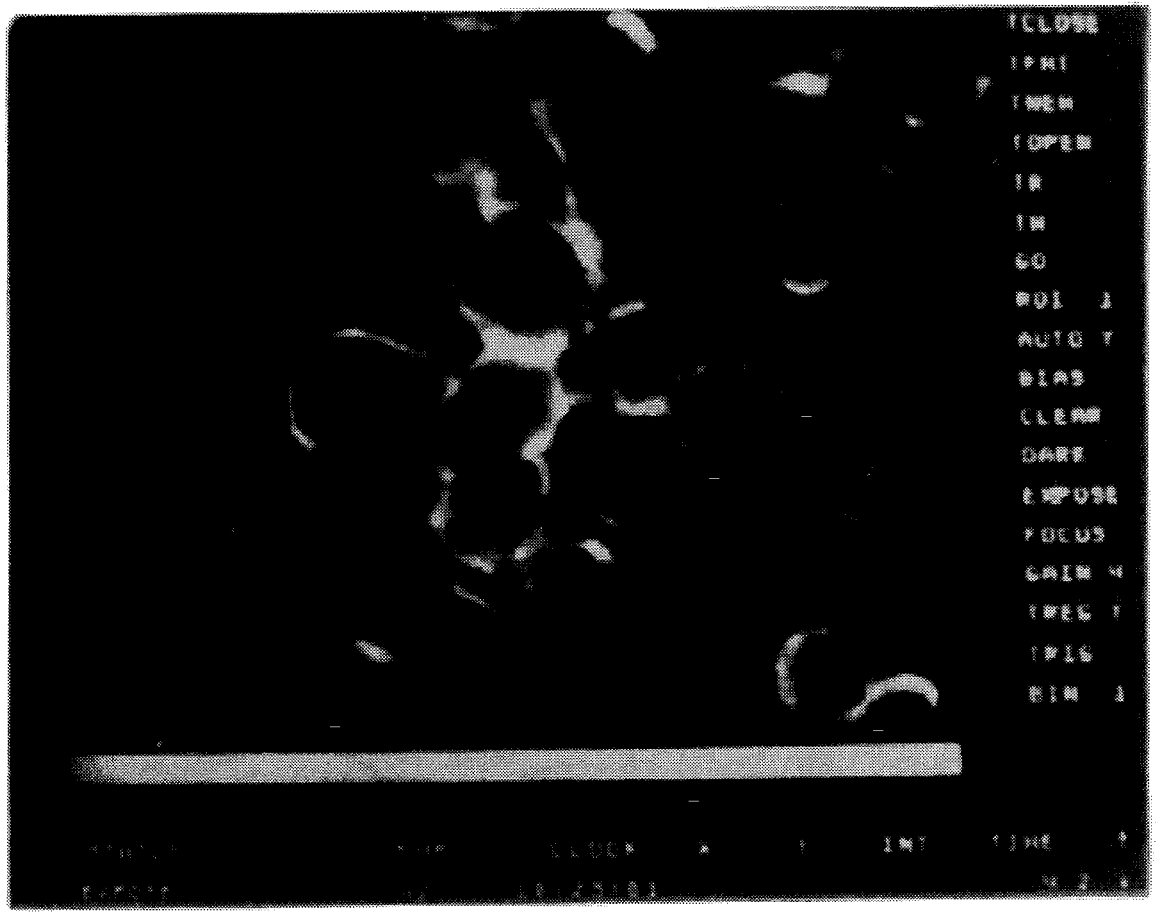
FIG. 4 is a photograph showing the reactivity of the antibody-bonded liposome (immuno liposome) prepared in Example 4 to human stomach cancer cells MKN45. The observation was made by a fluorescent microscope using a fluorescent lipid integrated to the liposome, as a marker.
Figure 5:
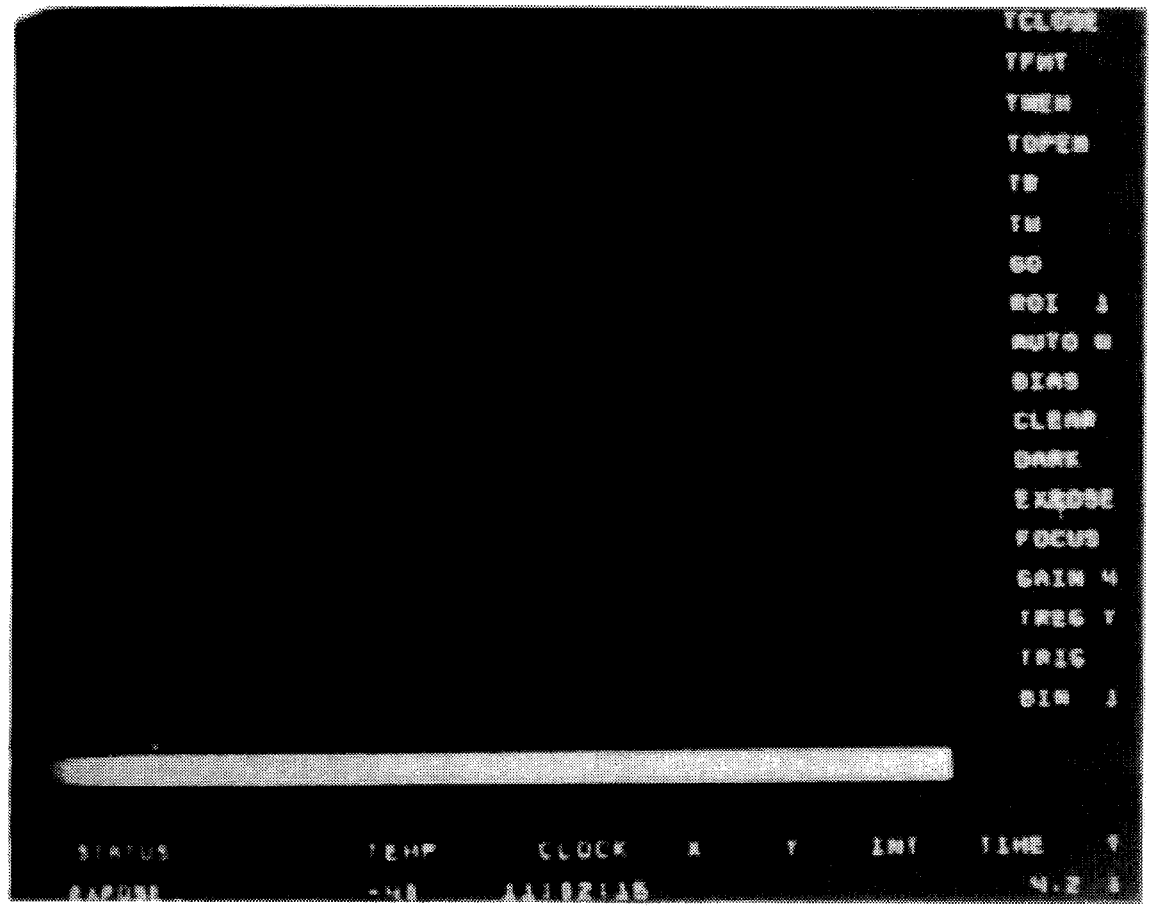
FIG. 5 is a photograph showing the reactivity of the non-antibody-bonded liposome prepared in Comparative Example to human stomach cancer cells MKN45. The observation was made by a fluorescent microscope using a fluorescent lipid integrated to the liposome, as a marker.
Figure 6:
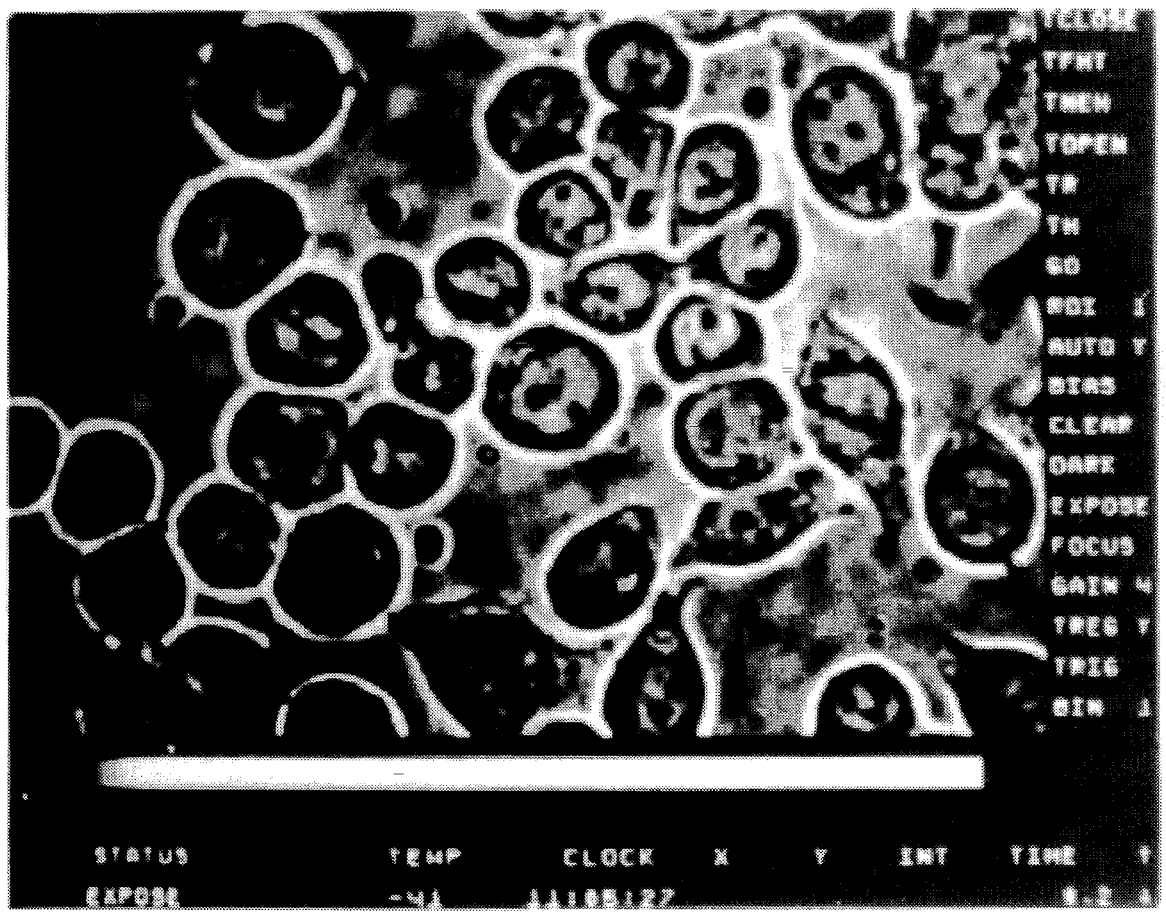
FIG. 6 is a photograph showing the luminous field image of FIG. 5.

Using human gastric cancer cell line MKN 45 (having a reactivity with the antibody used in Example 4) which was cultured on a slide chamber (LAB-TEK® chamber, manufactured by Nunc, Inc.) and fixed by paraformaldehyde, the reactivity of the immunoliposome prepared in Example 4, was confirmed. A reaction solution comprising 50 µl of the liposome solution, 150 µl of a human serum and 50 µl of a 10 mM phosphate buffer solution (pH 7.4) and 0.15M NaCl, was added to the cells, and the mixture was incubated at 37° C. for 30 minutes. After washing with the same buffer solution, fluorescence of FITC-DPPE (as mentioned above) introduced as a marker, was observed by a fluorescence microscope (Confocal microscope adoptor VX100, manufactured by Newport). The respective fluorescence microscopic photographs are shown in FIG. 4 (antibody-bonded liposome), FIG. 5 (non antibody-bonded liposome prepared in Comparative Example) and FIG. 6 (Luminous field image of FIG. 5). As compared with the liposome used as control, high reactivity of the immuno liposome of the present invention to MKN45 cells was confirmed.

The phospholipid derivative of the present invention is useful as a phospholipid component constituting a liposome, and the liposome employing the phospholipid derivative has a polyalkylene glycol moiety, whereby non-specific uptake by a recticuloendothelial system such as liver or spleen can be suppressed and at the same time the liposome can be readily bonded to a protein having thiol moiety. Further, by means of the phospholipid derivative of the present invention, the liposome can readily be micronized.

We claim:

1. A phospholipid derivative of formula (I):

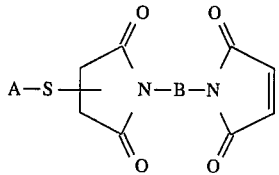 (I)

wherein A has the following formula (II):

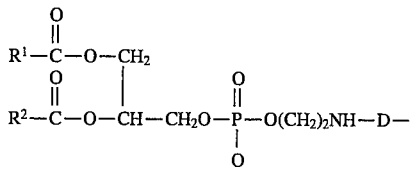 (II)

wherein each of $R^1$ and $R^2$, which are independent of each other, is a $C_{11}$–$C_{19}$ alkyl group or a $C_{11}$–$C_{19}$ alkenyl group, and D is a single bond, $-C=(NH_2^+)(CH_2)_{0-10}-$, $-CO(CH_2)_{0-10}-$ or $-CH_2(CH_2)_{0-10}-$, and B is a linking group having the following formula (III):

$$J\text{-}PEG\text{-}L \quad (III)$$

wherein each of J and L, which are independent of each other, is a single bond, $-CO(CH_2)_{0-10}-$, $-(CH_2)_{0-10}CO-$, $-NHCO(CH_2)_{0-10}-$, $-(CH_2)_{0-10}CONH-$ or $-CH_2(CH_2)_{0-10}-$, and PEG is a polyethylene glycol residue.

2. A liposome comprising the phospholipid derivative of claim 1.

3. The liposome according to claim 2 further comprising a drug.

4. The liposome according to claim 1, wherein a protein having a thiol group is reacted with a double bond of a maleimide group of the phospholipid derivative.

5. The liposome according to claim 4, wherein the protein having a thiol group is an antibody wherein endogenous dithiol groups in cysteine residues thereof have been reduced to thiol groups.

* * * * *